United States Patent [19]

Kiesele et al.

[11] Patent Number: 5,228,974

[45] Date of Patent: * Jul. 20, 1993

[54] ELECTROCHEMICAL MEASURING CELL FOR DETERMINING AMMONIA OR HYDRAZINE IN A MEASURING SAMPLE

[75] Inventors: Herbert Kiesele, Lübeck; Uwe Kühn, Wesenberg; Stephan Haupt, Lübeck, all of Fed. Rep. of Germany

[73] Assignee: Drägerwerk Aktiengesellschaft, Lübeck, Fed. Rep. of Germany

[*] Notice: The portion of the term of this patent subsequent to Dec. 31, 2008 has been disclaimed.

[21] Appl. No.: 804,722

[22] Filed: Dec. 11, 1991

Related U.S. Application Data

[63] Continuation-in-part of Ser. No. 507,755, Apr. 12, 1990, Pat. No. 5,076,904.

[30] Foreign Application Priority Data

Apr. 29, 1989 [DE] Fed. Rep. of Germany ....... 3914284

[51] Int. Cl.⁵ .......................................... G01N 27/404
[52] U.S. Cl. ............................... 204/415; 204/153.14; 204/153.2; 204/290 R; 204/291; 204/402
[58] Field of Search ...................... 204/153.14, 153.17, 204/153.2, 415, 431, 432, 290 R, 291, 402

[56] References Cited

U.S. PATENT DOCUMENTS

| | | | |
|---|---|---|---|
| 3,260,656 | 7/1966 | Ross | 204/415 |
| 3,515,658 | 6/1970 | Amdur | 204/415 |
| 3,830,718 | 8/1974 | Riseman et al. | 204/415 |
| 4,900,405 | 2/1990 | Otagawa et al. | 204/412 |

*Primary Examiner*—T. Tung
*Attorney, Agent, or Firm*—Walter Ottesen

[57] ABSTRACT

The invention is directed to an electrochemical measuring cell for measuring ammonia or hydrazine and includes at least a measuring electrode and a counter electrode in an electrolyte. The measuring cell provides a signal increase having a shorter response time and an improved signal stability. For this purpose, the electrolyte is an aqueous solution of a hygroscopic salt of an alkali metal or earth alkali metal such as calcium nitrate or lithium nitrate or a mixture of both salts.

23 Claims, 1 Drawing Sheet

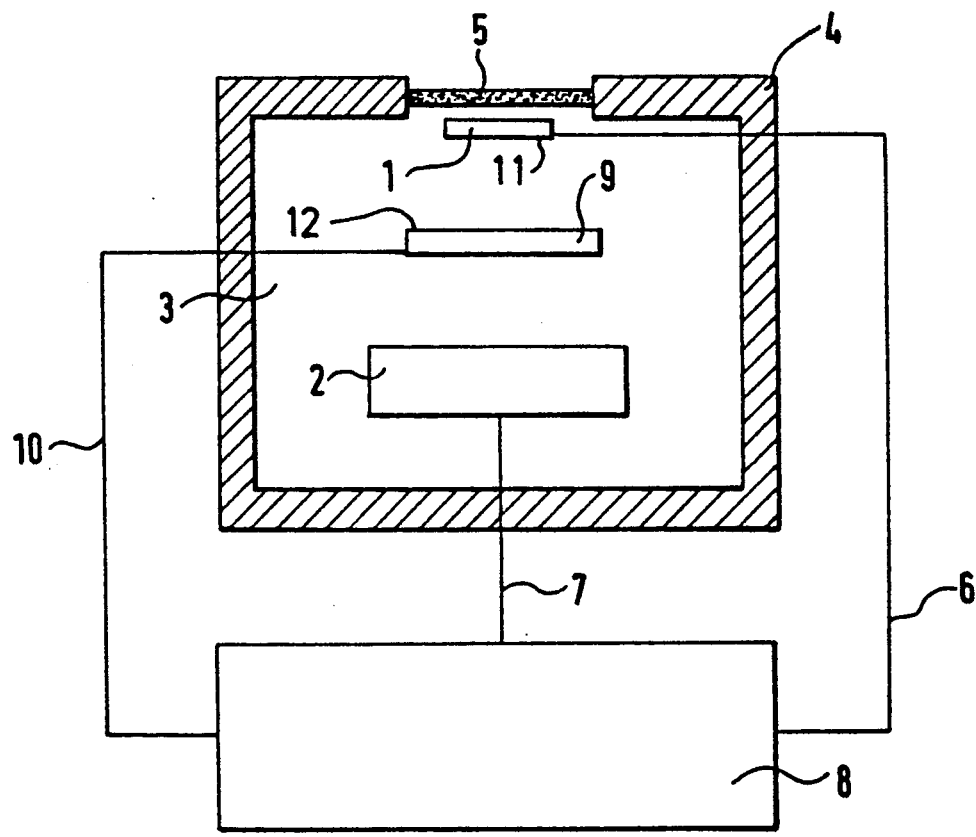

ELECTROCHEMICAL MEASURING CELL FOR DETERMINING AMMONIA OR HYDRAZINE IN A MEASURING SAMPLE

RELATED APPLICATION

This is a continuation-in-part of application Ser. No. 507,755, filed Apr. 12, 1990, which has issued as U.S. Pat. No. 5,076,904.

FIELD OF THE INVENTION

The invention relates to an electrochemical measuring cell for determining ammonia or hydrazine in a fluid (gaseous or liquid) measuring sample. The measuring cell has at least one measuring electrode and at least one counter electrode which are arranged in an electrolyte chamber filled with a soluble electrolyte. The electrolyte chamber is closed off with respect to the measuring sample by a permeable membrane.

BACKGROUND OF THE INVENTION

An electrochemical measuring cell of this kind is disclosed in U.S. Pat. No. 3,649,505 and includes a pH-electrode as a measuring electrode which is used to measure hydrogen ions. This potentiometric measurement of an ammonia concentration requires a long time duration for a completed measuring reaction. The long time duration is needed for the adjustment of an equilibrium. In this time duration, the $NH_3$ to be detected and the water content of the electrolyte conjointly form $NH_4OH$ which, in turn, dissociates into $NH_4^+$ ions and $OH^-$ ions. The slow step determining the speed for this reaction is the adjustment of the equilibrium with the gas space or the adjustment of the equilibrium at the glass membrane.

The glass electrode required for the pH-measurement changes in the characteristic of the glass membrane in the course of its use so that drift phenomena occur. A stable reference potential is necessary for carrying out the pH-measurement and a displacement of this reference potential in the course of use likewise leads to drift phenomena. The known measuring cell responds to all gases influencing the pH-value of the electrolyte so that its selectivity for measurements in corresponding gas mixtures is not adequate.

SUMMARY OF THE INVENTION

It is an object of the invention to provide an electrochemical measuring cell of the kind described above which is improved so that a selective ammonia measurement is obtained providing the following: short response time, a linear response and a low tendency to drift. It is a further object of the invention to provide such an electrochemical measuring cell having electrodes which are so configured that the oxidation of the ammonia or hydrazine as a measurement reaction has no influence on the sensitivity of this measuring cell.

The electrochemical measuring cell of the invention is for determining ammonia or hydrazine in a fluid measuring sample. The measuring cell includes: a housing having an opening directed toward the sample to be measured and defining an electrolyte chamber; a soluble electrolyte contained in the chamber; a permeable membrane mounted on the housing for closing off the chamber; a measuring electrode and a counter electrode disposed in the chamber so as to be in spaced relationship to each other; and, the measuring electrode having a coating containing cobalt oxide and the coating being formed on the measuring electrode so as to be in direct contact with the electrolyte.

The advantage of the invention is essentially that the oxidation of the ammonia at the measuring electrode is catalyzed by the cobalt oxide coating so that no disturbing secondary products develop at the measuring electrode which could hinder an oxidation which follows. Furthermore, no blocking of the electrode occurs because of an electrochemically inert passive layer.

The measuring cell according to the invention affords the advantage that it offers a very good long-term stability and negligible drift. Also, very high concentrations of ammonia can be measured because of the catalytically effective oxide layer. These high concentrations are rendered harmless with respect to catalytic poisons or disadvantageous influences of the electrolyte for the operational capability of the measuring cell. Because of the coating of cobalt oxide, the oxidation of ammonia at the measuring electrode surface occurs so rapidly that the ammonia concentration at this electrode surface is practically zero. This results in a high concentration gradient between the measuring sample and the surface of the measuring electrode. In this way, the measuring cell reaction is returned to a transport-controlled reaction without restrictive reaction steps. This leads to a rapid response time and to a high sensitivity of the measuring cell. Gold, platinum or iridium can be selected as a carrier material for the electrode. The measuring cell of the invention is equally well suited for detecting hydrazine.

For producing a cobalt oxide coating, a carrier material of gold defining the electrode can, for example, be dipped into a cobalt nitrate solution or a cobalt acetate solution and cobalt oxide is then electrically deposited thereon. Potassium nitrate can be added to the cobalt solution as a conductive electrolyte. Another method for forming the cobalt oxide coating is to form the carrier material for the electrode from a cobalt-containing alloy which is then oxidized.

Carrier materials for electrochemically measuring ammonia can be used by applying the coating containing cobalt oxide. Without this coating, a surface passivation in the form of a nitride formation occurs whereby the measuring sensitivity is reduced to the point that the measuring cell is unusable. In this connection, reference may be made to the "Encyclopedia of Electrochemistry of the Elements", Volume 8, 1978, page 413.

With respect to the measuring cell of the invention, it is emphasized that there is no cross-sensitivity against carbon monoxide or hydrogen.

In order to generate a reference potential for determining ammonia or hydrazine, a reference electrode is introduced into the measuring cell having a potential which functions as a reference point for the measurement. It is advantageous to likewise provide such a reference electrode with a coating containing cobalt oxide. A measuring cell of this kind affords the advantage that it can be stored with short-circuited electrodes whereby it is immediately operationally ready because of the short warm-up time. Furthermore, the dependency of the residual current on temperature is minimized since the potential of the measuring electrode and of the reference electrode are influenced in the same manner by the temperature.

U.S. Pat. No. 5,076,904 discloses a measuring cell wherein the $NH_3$ molecules diffuse from the gas phase through the porous membrane and a thin electrolyte film to the electrode where they are anodically oxidized. The permeability of the gas to be measured in the electrolyte film is essential for a high sensitivity of the sensor. The minimum operating temperature of the sensor is limited by the freezing point of the electrolyte while the service life of the sensor is determined primarily by the water vapor pressure of the electrolyte.

Accordingly, it is still another object of the invention to improve a measuring cell of the kind described in the above-mentioned European patent application to increase the sensitivity as well as to lower the operating temperature and increase the service life.

The above object is achieved by providing as an electrolyte, an aqueous solution of a hygroscopic salt of an alkali metal or an earth alkali metal or a mixture of both salts.

The hygroscopic salts effect a reduction of the freezing point so that the sensors can be utilized down to a temperature of $-50°$ C. in refrigerating plants or in open air. The water vapor pressure of the electrolyte solution is reduced so that the liquid loss is slowed and a large electrolyte reservoir is unnecessary.

If, as an example, a hygroscopic salt such as lithium nitrate, magnesium nitrate or calcium nitrate or a mixture of these salts is selected, then ammonia and hydrazine form complexes or complex-type bonds with the cations. In this way, the solubility and the permeability and therefore the sensitivity is increased.

To further improve the electrochemical measuring cell, it is advantageous to provide the measuring electrode with a coating containing cobalt oxide with the coating being so applied on the measuring electrode that the electrode is in direct contact with the electrolyte. An improved protection of the measuring electrode surface against disturbing reactions of reaction products is obtained with the cobalt oxide coating.

If a so-called three-electrode measuring cell is utilized, then it is advantageous to provide a reference electrode in the electrolyte which likewise has a coating containing cobalt oxide.

The measuring electrode and reference electrode can preferably be made of a precious metal such as gold with the coating being deposited electrolytically on the carrier material of the electrode.

It can be just as advantageous to produce the measuring electrode and the reference electrode from a carrier which comprises a cobalt alloy and with the coating being formed from an oxide layer which is obtained by oxidation of the alloy.

For an electrode material having a cobalt oxide coating, it is advantageous to add a soluble cobalt salt to the electrolyte. The cobalt salt acts as a catalyzer in that it regenerates the cobalt oxide coating if the coating should become damaged during operation of the measuring cell. Furthermore, the cobalt salt supports the catalytic reaction of the ammonia oxidation or hydrazine oxidation at the measuring electrode in the electrolyte. In this way, the sensitivity and the response speed of the chemical measuring cell are increased.

An advantageous cobalt salt for this purpose is cobalt nitrate. By using the cobalt salt and especially cobalt nitrate, the generation of a new cobalt oxide layer is favored insofar as it is attacked by a chemical disturbance reaction. An especially suitable mixture for the electrolyte is a 3.5 molar solution of calcium nitrate or lithium nitrate and a 0.1 millimolar cobalt nitrate admixture as a catalyzer. The admixture of cobalt nitrate can be increased up to 1 millimol without the detection function of the measuring cell being affected.

It is emphasized that the electrochemical measuring cell of the invention has no cross sensitivity with respect to carbon monoxide and hydrogen.

A reference electrode is introduced into the measuring cell to generate a reference potential for the determination of ammonia or hydrazine. The potential of the reference electrode defines a reference point for the measurement. It is advantageous to likewise provide such a reference electrode with a coating containing cobalt oxide.

A measuring cell of this kind affords the advantage that the cell can be stored with its electrodes short circuited whereby the cell is immediately operationally ready because of the short run-in time. Furthermore, the dependence of the base current on the temperature is minimized since the potential of the measuring electrode and the reference electrode is influenced in the same manner by the temperature.

BRIEF DESCRIPTION OF THE DRAWING

The invention will now be described with reference to the single figure of the drawing which is a side elevation view, in section, of a measuring cell according to the invention.

DESCRIPTION OF THE PREFERRED EMBODIMENTS OF THE INVENTION

The electrochemical measuring cell includes an electrolyte 3 of an aqueous solution of calcium nitrate and lithium nitrate. The electrolyte is contained in a housing 4 in which a measuring electrode 1, a counter electrode 2 and a reference electrode 9 are introduced. The electrodes (1, 9) have respective coatings (11, 12) containing cobalt oxide. The electrolyte 3 is closed off in a direction facing toward the ambient containing the measuring sample by a membrane 5 which is permeable to ammonia and hydrazine and which is attached to the housing 4 in a seal-tight manner. The measuring electrode 1, the counter electrode 2 and the reference electrode 9 have respective measurement leads (6, 7, 10) which are passed through the housing 4 and connected to an evaluation device 8 for processing the measurement signals.

It is understood that the foregoing description is that of the preferred embodiments of the invention and that various changes and modifications may be made thereto without departing from the spirit and scope of the invention as defined in the appended claims.

What is claimed is:

1. An electrochemical measuring cell for determining ammonia or hydrazine in a fluid measuring sample present in the abient, the measuring cell comprising:

a housing having an opening directed toward the sample to be measured and defining an electrolyte chamber;

a soluble electrolyte contained in said chamber;

a membrane mounted on said housing for closing off said chamber to the ambient and being permeable to ammonia and hydrazine;

a measuring electrode and a counter electrode disposed in said chamber so as to be in spaced relationship to each other;

said soluble electrolyte being an aqueous solution of a hygroscopic salt of an alkali metal; and, said measuring electrode having a cobalt oxide coating; and, said coating being formed on said measuring electrode so as to be in direct contact with said electrolyte.

2. The electrochemical measuring cell of claim 1, further comprising a reference electrode disposed in said electrolyte and having a coating containing cobalt oxide formed thereon.

3. The electrochemical measuring cell of claim 1, further comprising a reference electrode disposed in said electrolyte; and, at least one of said measuring electrode and said reference electrode each including a carrier made of a noble metal and said coating being electrolytically deposited on said carrier.

4. The electrochemical measuring cell of claim 1, further comprising a reference electrode disposed in said electrolyte; and, at least one of said measuring electrode and said reference electrode including a carrier containing a cobalt alloy and said coating being an oxide layer formed by oxidizing said alloy.

5. An electrochemical measuring cell for determining ammonia or hydrazine in a fluid measuring sample present in the ambient, the measuring cell comprising:
- a housing having an opening directed toward the sample to be measured and defining an electrolyte chamber;
- a soluble electrolyte contained in said chamber;
- a membrane mounted on said housing for closing off said chamber to the ambient and being permeable to ammonia and hydrazine;
- a measuring electrode and a counter electrode disposed in said chamber so as to be in spaced relationship to each other;
- said soluble electrolyte being an aqueous solution of a hygroscopic salt of an alkali metal; and,
- said electrolyte including a cobalt salt dissolved therein.

6. The electrochemical measuring cell of claim 5, said cobalt salt being cobalt nitrate.

7. An electrochemical measuring cell for determining ammonia or hydrazine in a fluid measuring sample present in the ambient, the measuring cell comprising:
- a housing having an opening directed toward the sample to be measured and defining an electrolyte chamber;
- a soluble electrolyte contained in said chamber;
- a membrane mounted on said housing for closing off said chamber to the ambient and being permeable to ammonia and hydrazine;
- a measuring electrode and a counter electrode disposed in said chamber so as to be in spaced relationship to each other;
- said soluble electrolyte being an aqueous solution of a hygroscopic salt of an alkaline earth metal; and,
- said hygroscopic salt having a concentration in said aqueous solution for obtaining a reduction of the freezing point of said solution down to a temperature of $-50°$ C.

8. The electrochemical measuring cell of claim 7, wherein said hygroscopic salt has a cationic component and an anionic component; said cationic component being selected from the group consisting of magnesium and calcium; and, said anionic component being selected from the group consisting of a nitrate and chloride.

9. An electrochemical measuring cell for determining ammonia or hydrazine in a fluid measuring sample present in the ambient, the measuring cell comprising:
- a housing having an opening directed toward the sample to be measured and defining an electrolyte chamber;
- a soluble electrolyte contained in said chamber;
- a membrane mounted on said housing for closing off said chamber to the ambient and being permeable to ammonia and hydrazine;
- a measuring electrode and a counter electrode disposed in said chamber so as to be in spaced relationship to each other;
- said soluble electrolyte being an aqueous solution of a hygroscopic salt of an alkaline earth metal; and,
- said measuring electrode having a cobalt oxide coating; and, said coating being formed on said measuring electrode so as to be in direct contact with said electrolyte.

10. The electrochemical measuring cell of claim 9, further comprising a reference electrode disposed in said electrolyte and having a coating containing cobalt oxide formed thereon.

11. The electrochemical measuring cell of claim 9, further comprising a reference electrode disposed in said electrolyte; and, at least one of said measuring electrode and said reference electrode each including a carrier made of a noble metal and said coating being electrolytically deposited on said carrier.

12. The electrochemical measuring cell of claim 9, further comprising a reference electrode disposed in said electrolyte; and, at least one of said measuring electrode and said reference electrode including a carrier containing a cobalt alloy and said coating being an oxide layer formed by oxidizing said alloy.

13. An electrochemical measuring cell for determining ammonia or hydrazine in a fluid measuring sample present in the ambient, the measuring cell comprising:
- a housing having an opening directed toward the sample to be measured and defining an electrolyte chamber;
- a soluble electrolyte contained in said chamber;
- a membrane mounted on said housing for closing off said chamber to the ambient and being permeable to ammonia and hydrazine;
- a measuring electrode and a counter electrode disposed in said chamber so as to be in spaced relationship to each other;
- said soluble electrolyte being an aqueous solution of a hygroscopic salt of an alkaline earth metal; and,
- said electrolyte including a cobalt salt dissolved therein.

14. The electrochemical measuring cell of claim 13, said cobalt salt being cobalt nitrate.

15. An electrochemical measuring cell for determining ammonia or hydrazine in a fluid measuring sample present in the ambient, the measuring cell comprising:
- a housing having an opening directed toward the sample to be measured and defining an electrolyte chamber;
- a soluble electrolyte contained in said chamber;
- a membrane mounted on said housing for closing off said chamber to the ambient and being permeable to ammonia and hydrazine;
- a measuring electrode and a counter electrode disposed in said chamber so as to be in spaced relationship to each other; and,
- said soluble electrolyte being an aqueous solution of a mixture of a hygroscopic salt of an alkali metal and a hygroscopic salt of an alkaline earth metal.

16. The electrochemical measuring cell of claim 15, wherein said salt of said alkali metal has a cationic component and an anionic component; said cationic component being lithium; said salt of said alkaline earth metal has a cationic component and a anionic component; said cationic component being selected from the group consisting of magnesium and calcium; and, said anionic component being selected from the group consisting of a nitrate and chloride.

17. The electrochemical measuring cell of claim 15, said measuring electrode having a cobalt oxide coating; and, said coating being formed on said measuring electrode so as to be in direct contact with said electrolyte.

18. The electrochemical measuring cell of claim 17, further comprising a reference electrode disposed in said electrolyte and having a coating containing cobalt oxide formed thereon.

19. The electrochemical measuring cell of claim 17, further comprising a reference electrode disposed in said electrolyte; and, at least one of said measuring electrode and said reference electrode each including a carrier made of a noble metal and said coating being electrolytically deposited on said carrier.

20. The electrochemical measuring cell of claim 17, further comprising a reference electrode disposed in said electrolyte; and, at least one of said measuring electrode and said reference electrode including a carrier containing a cobalt alloy and said coating being an oxide layer formed by oxidizing said alloy.

21. The electrochemical measuring cell of claim 15, said electrolyte including a cobalt salt dissolved therein.

22. The electrochemical measuring cell of claim 21, said cobalt salt being cobalt nitrate.

23. The electrochemical measuring cell of claim 15, said mixture having a concentration in said aqueous solution for obtaining a reduction of the freezing point of said solution down to a temperature of $-50°$ C.

* * * * *

UNITED STATES PATENT AND TRADEMARK OFFICE
CERTIFICATE OF CORRECTION

PATENT NO. : 5,228,974

DATED : July 20, 1993

INVENTOR(S) : Herbert Kiesele, Uwe Kühn and Stephan Haupt

It is certified that error appears in the above-identified patent and that said Letters Patent is hereby corrected as shown below:

In column 3, line 10: delete " European patent application" and substitute -- U.S. Pat. No. 5,076,904 --.

In column 4, line 54: delete "abient" and substitute -- ambient -- therefor,

In column 7, line 5: delete "a" (second occurrence) and substitute -- an -- therefor, Signed and Sealed this Twenty-eighth Day of June, 1994

Attest:

BRUCE LEHMAN

*Attesting Officer*     *Commissioner of Patents and Trademarks*